United States Patent [19]

Neumeyer et al.

[11] 4,053,603
[45] Oct. 11, 1977

[54] BENZYLISOQUINOLINE DERIVATIVES, AND USE AS ANTI-ARRHYTHMIC DRUGS

[75] Inventors: John Leopold Neumeyer, Wayland; Paul Andre Tenthorey, Holden, both of Mass.

[73] Assignee: Astra Pharmaceutical Products, Inc., Worcester, Mass.

[21] Appl. No.: 704,096

[22] Filed: July 9, 1976

[51] Int. Cl.$^2$ .................. A61K 31/485; C07D 217/20
[52] U.S. Cl. .............................. 424/258; 260/287 D; 260/544 Y; 260/612 R
[58] Field of Search .................... 260/287 D; 424/258

[56] References Cited

U.S. PATENT DOCUMENTS

| | | | |
|---|---|---|---|
| 2,634,292 | 4/1953 | Hellerbach | 260/287 D |
| 3,579,502 | 5/1971 | Muller et al. | 260/287 D |
| 3,717,639 | 2/1973 | Neumeyer | 424/258 |
| 3,946,018 | 3/1976 | Deak et al. | 260/287 D |

*Primary Examiner*—Donald G. Daus
*Assistant Examiner*—David E. Wheeler

*Attorney, Agent, or Firm*—Brumbaugh, Graves, Donohue & Raymond

[57] ABSTRACT

Compounds of the class of benzylisoquinoline derivatives of the formula

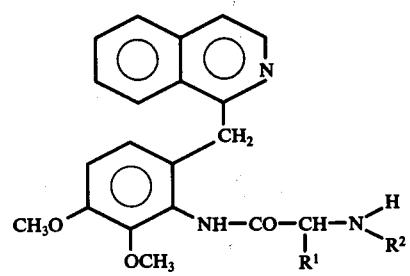

wherein $R^1$ is selected from the group consisting of hydrogen and methyl, and $R^2$ is selected from the group consisting of methyl, ethyl, n-propyl and isopropyl, and therapeutically acceptable salts thereof, useful as active ingredients of pharmaceutical preparations for the treatment of cardiac arrhythmias.

27 Claims, No Drawings

BENZYLISOQUINOLINE DERIVATIVES, AND USE AS ANTI-ARRHYTHMIC DRUGS

BACKGROUND OF THE INVENTION

The present invention relates to new benzylisoquinoline derivatives which have been shown to be effective as antiarrhythmic agents. The isoquinoline derivative papaverine has found use as a smooth muscle relaxant and antispasmodic. Its actions on the heart to depress conduction and irritability of the myocardium served as a basis for its clinical use in abrogating atrial and ventricular extrasystoles and ventricular arrhythmias, but doses required were also found to cause dangerous arrhythmias by depression of A-V and intraventricular conduction. Accordingly, this class of compound has not found effective application in this indication.

Drugs such as quinidine, procainamide, propanolol and diphenylhydantoin have found significant application as antiarrhythmics, as has particularly the local anesthetic lidocaine (2-diethylamino-2',6'-acetoxylidide) which has proved effective as an antiarrhythmic drug administered both intravenously and intramuscularly. The use of 1-(2',6'-dimethylphenoxy)-2-amino propane has also been studied. Other classes of known drugs which exhibit antiarrhythmic properties are the 2-amino tetralins, and also certain primary amino acylanilides which have shown effectiveness both on parenteral and oral administration.

SUMMARY OF THE INVENTION

Particularly, this invention is directed to a compound having the structure

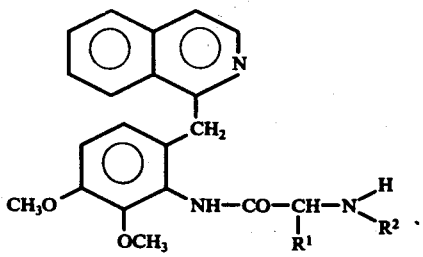

in which $R^1$ may be hydrogen or methyl, and $R^2$ may be methyl, ethyl, n-propyl or isopropyl, therapeutically acceptable salts thereof, and pharmaceutical compositions containing the same.

It is superior to the isoquinoline compound papaverine with respect to antiarrhythmic properties, and protects against chloroform induced fibrillation and abolishes arrhythmias in the coronary-ligated dog at nontoxic doses.

The final products of this invention are physiologically active substances which are useful as antiarrhythmic agents, and accordingly they may be administered to mammals in lieu of known antiarrhythmic agents such as lidocaine, quinidine, porcainamide and the like.

The compounds may be formulated for such administration based on the activity of the particular compound and the requirements of the patient using conventional pharmaceutically acceptable carriers.

As the compounds of the invention of the formula I possess at least one asymmetric carbon atom, the invention also incudes all the possible optically active forms and racemic mixtures of the compounds. The racemic mixtures may be resolved by conventional methods, for example, by salt formation with an optically active acid, followed by fractional crystallization.

The compounds of the invention may be formulated for use in human and veterinary medicine for therapeutic and prophylactic use. Generally, they will be used in the form of a therapeutically acceptable salt such as the hydrochloride, sulfate, maleate, tartrate, etc.

In clinical practice the compounds of the present invention will normally be administered orally or by injection in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. Usually the active substance will comprise between 0.1 and 99% by weight of the preparation, for example, between 0.5 and 20% for preparations intended for injection and between 5 and 99% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragees. If dragees are required, the cores may be coated, for example with concentrated sugar solutions which may contain gum arabic, talc and/or titanium dioxide, or alternatively with a film-forming agent dissolved in easily volatilized organic solvents or mixtures of organic solvents. Dyestuffs can be added to these coatings, for example, to distinguish between different contents of active substance. For the preparation of soft gelatin capsules (pearl-shaped closed capsules) consisting of gelatin and, for example, glycerol as a plasticizer, or similar closed capsules, the active substance may be admixed with a Carbowax ® or suitable oil such as, for example, sesame oil, olive oil or arachis oil. Hard gelatin capsules may contain granulates of the active substance with solid, pulverulent carriers such as lactose, saccharose, sorbitol, mannitol, starches (for example potato starch, corn starch or amylopectin), cellulose derivatives or gelatin, and may also include magnesium stearate or stearic acid as lubricants.

By using several layers of the active drug, separated by slowly dissolving coatings, sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made, for instance, of fat and wax substances, or evenly distributed in a tablet of an insoluble substance such as a physiologically inert plastic.

Effervescent powders are prepared by mixing the active ingredient with non-toxic carbonates or hydrogen carbonates of, for example, sodium, potassium or calcium, such as calcium carbonate, potassium carbonate and potassium hydrogen carbonate, solid, non-toxic acids such as tartaric acid, ascorbic acid, and citric acid.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally flavoring agents, saccharine and/or carboxymethylcellulose as a dispersing agent.

For parenteral application by injection, preparations may comprise an aqueous solution of a water soluble, pharmaceutically acceptable salt of the active acids according to the invention, desirably in a concentration of 0.5 - 10%, and optionally also a stabilizing agent and/or buffer substances in aqueous solution. Dosage units of the solution may advantageously be enclosed in ampoules or vials.

The pharmaceutical compositions containing the active ingredients may suitably be formulated so that they provide such doses either as single dosage units or as multiple dosage units.

DESCRIPTION OF PROCESSES FOR PREPARING THE COMPOUNDS

The compounds of the invention may be prepared by known methods such as by

A. reacting a compound of the formula

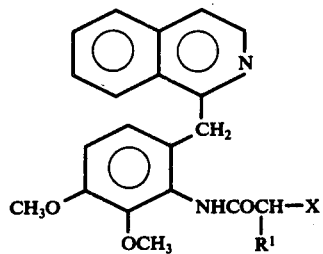

II wherein $R^1$ is selected from the group consisting of hydrogen and methyl, and wherein X is a halogen atom such as Cl or Br, or a functionally equivalent derivative thereof, with a compound of the formula

III wherein $R^2$ is selected from the group consisting of methyl, ethyl, n-propyl and isopropyl, to form a compound of the formula

I

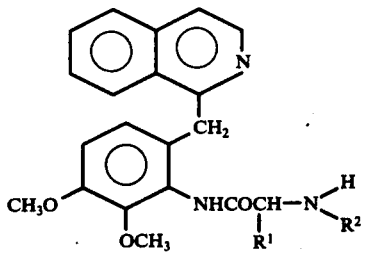

wherein $R^1$ and $R^2$ have the meaning given above. If necessary, the amino groups may be protected during the process in manner known in the art.

B. reacting a compound of the formula

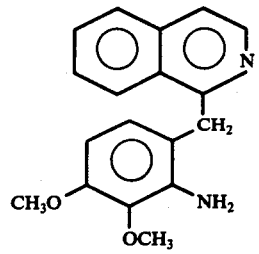

VIII with a compound of the formula

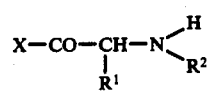

IX wherein $R_1$ and $R_2$ have the meaning given above and X is halogen or a functionally equivalent group, to form a compound of the formula I.

If necessary, the amino groups may be protected during the process in manner known in the art.

C. alkylation of the amino group in the compound of the formula

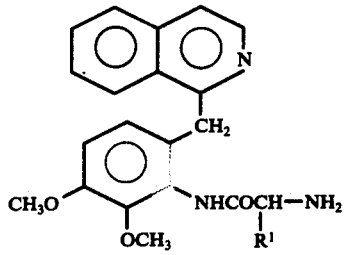

for example, by reaction with acetaldehyde and reduction to the ethylamino derivative.

D. reaction of a compound of the formula

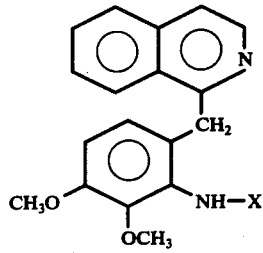

and a suitably protected amino acid

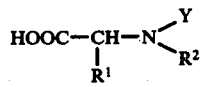

wherein Y is the protecting group, with the help of a coupling agent such as, for example, dicyclohexyl carbodiimide, to form

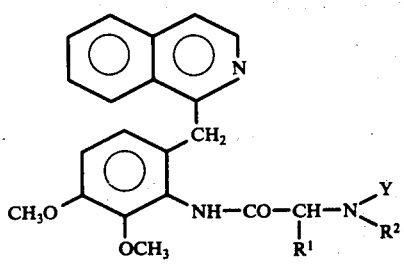

from which the secondary amine can be liberated.

The starting materials may be obtained according to the following reaction scheme:

A procedure leading via compounding VIII to a compound II wherein $R^1$ is H, and $X'$ is Cl is exemplified in Example 1 (A), (B) and (C) (infra).

The process A is exemplified in Example 1 (E) (infra).

The compounds of the invention may be prepared according to the procedure of Neumeyer et al. in J. Med. Chem. 16, 1223 (1973) as described in U.S. Pat. No. 3,717,639 of Neumeyer, involving, as for example reactions of the Reissert derivative of isoquinoline with a nitrobenzyl halide to form a 1-nitrobenzyl isoquinoline derivative, followed by reduction of the nitro group to the amine. This may, in turn, be reacted with halo acyl halides to form the corresponding halo amides, from which, by amination, the desired compounds are obtained. It can be appreciated that alternative procedures within the general framework may likewise be employed.

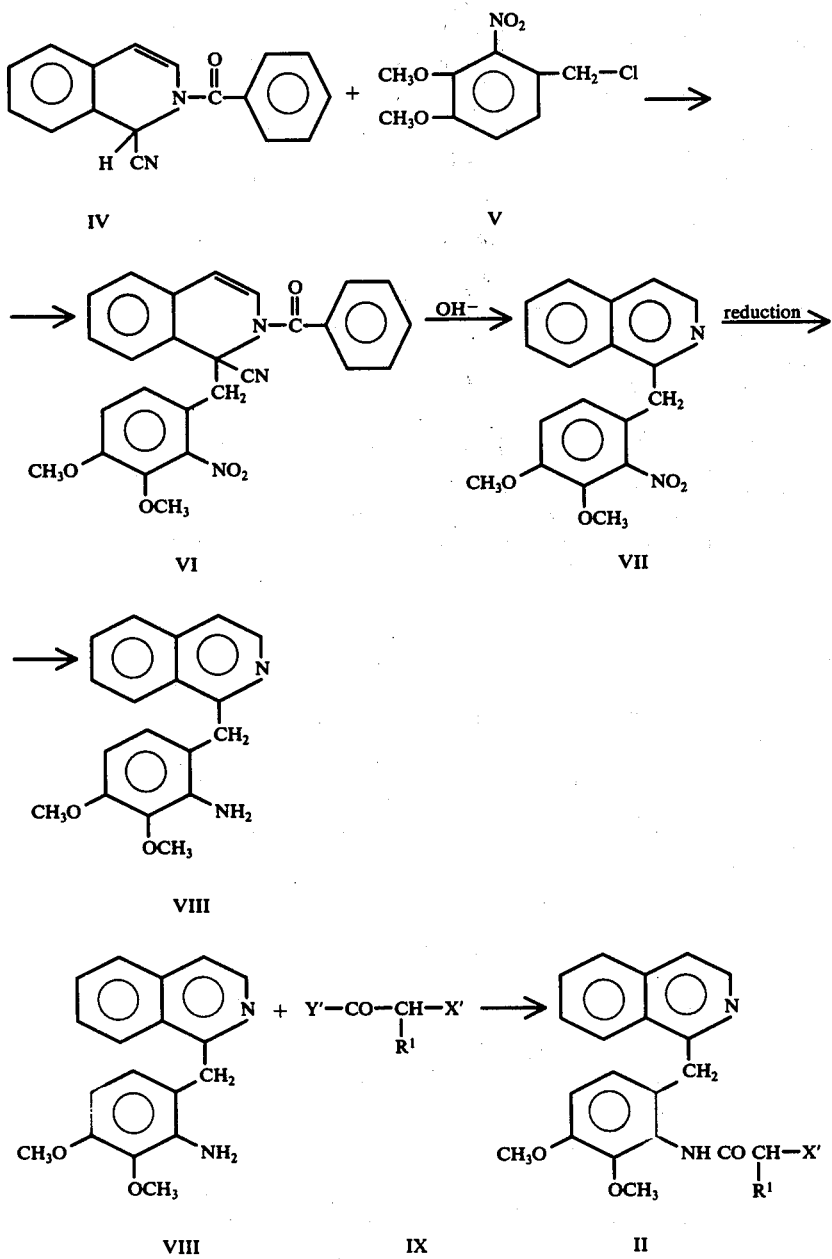

The radicals $X'$ and $Y'$ are halogen such as Cl or Br or functionally equivalent groups.

If necessary, the amino groups may be protected during the processes as is recognized in the art.

The following non-limiting examples illustrate the invention:

EXAMPLE 1

1-(2-[2-ethylamino-acetyl]amino-3,4-dimethoxybenzyl)isoquinoline

A. 1-(3,4-dimethoxy-2-nitrobenzyl) isoquinoline was obtained by reaction of 2-benzoyl-1,2-dihydroisoquinaldonitrile and α-chloro-3,4-dimethoxy-2-nitrotoluene, m.p. 127°–128°.

B. Reduction of the 1-nitrobenzyl-isoquinoline derivative obtained above was effected by dissolving 13.6 g (0.042 mole) in 400 ml. of hot ethanol and 80 ml. of water, and incorporating 300 mg. of 10% palladium on carbon. KBH$_4$ was then added in four 1.5 g portions at 10 minute intervals. The mixture was stirred at room temperature for 2 hours, and then filtered through a celite pad. The recovered palladium on carbon was washed thoroughly with methylene chloride. The organic layer was separated and concentrated to dryness, following which the residue was recrystallized from ethanol yielding 10.4g (83%) of 1-(2-amino-3,4-dimethoxybenzyl) isoquinoline; mp 90°–91°; $_{max}^{KBr}$ 3380 cm$^{-1}$ (—NH); $\delta_{tms}^{CDCl_3}$ 1.10 (broad s, 2,NH$_2$); 3.53 (s,3,OCH$_3$), 3.60 (s,3,OCH$_3$), 4.27 (s,2,CH$_2$), 6.00 (d, J=8.0 Hz, 1, aromatic), 6.80 (d, J=8.0 Hz, 1, aromatic), 7.00–7.50 (m,4, aromatic) and 8.00–8.25 (m,2, aromatic).

C. 1-(2-[2-chloro-acetyl]amino-3,4-dimethoxybenzyl)isoquinoline was prepared from 5.9g (0.02 mol) of 1-(2-amino-3,4-dimethoxybenzyl) isoquinoline dissolved in 400 ml. of ethyl acetate, and stirred for 2 hours with 15 ml. of chloro-acetyl chloride. The precipitate which formed was filtered and dried to yield 7.1g (87%) of the hydrochloride salt, mp 193°–194°, which was suspended in 200 ml. of water and stirred for 10 min. with 10% Na$_2$CO$_3$ solution. The free base was extracted with chloroform, and the organic layer was washed with water, dried (sodium sulfate) and concentrated to yield a residue which was crystallized from methanol to give the pure base; mp 166°–167°; $_{max}^{KBR}$ 1650 cm$^{-1}$ (aminde C=O); $\delta_{tms}^{CDCl_3}$ 3.75 (s, 3, OCH$_3$), 3.90 (s, 3, OCH$_3$), 4.20 (s, 2, CH$_2$Cl), 4.55 (s, 2, CH$_2$), 6.63–7.00 (m, 2, aromatic), 7.23–7.85 (m, 4, aromatic), 8.20–8.45 (m, 2 aromatic) and 9.80 (broad s, 1, NH).

Analysis: (C$_{20}$H$_{19}$ClN$_2$O$_3$). Calculated (percent): C=64.78; H=5.16; N=7.55. Found (percent): C=64.44; H=5.31; N=7.46.

D. By the same procedure, 1-(2[2-chloro-propionyl]-amino-3,4-dimethoxybenzyl) isoquinoline was prepared from 1-(2-amino-3,4-dimethoxybenzyl) isoquinoline and 2-chloropropionyl chloride, yielding 6.2g (92%) of the hydrochloride salt, mp 199°–200°, from which 4.5g (73%) of the base, mp 162°–163°, was liberated.

Analysis: (C$_{21}$H$_{21}$ClN$_2$O$_3$). Calculated (percent): C=65.54; H=5.50; N=7.28. Found (percent): C=65.25; H=5.78; N=7.17.

E. 1-(2-[2-ethylamino-acetyl]amino-3,4-dimethoxybenzyl) isoquinoline, which represents a preferred embodiment of the invention, was prepared from a mixture of 1.85g (0.005 mol) of 1-(2-[2-chloro-acetyl]amino-3,4-dimethoxybenzyl) isoquinoline, 20 ml. of ethylamine, and 150 ml. of benzene. The mixture was refluxed for 3 hours, the solvent removed, and the pale yellow residue which remained was triturated with hexane and filtered to yield 1.4g of a colorless powder. The crude product was then triturated with water, filtered, washed with water and dried. This was then recrystallized from isopropanol to yield 1.3g (68%) of base, mp 107°–108°; $_{max}^{KBr}$3280 cm$^{-1}$(NH) and 1670 cm$^{-1}$(amide C=O) and $\delta_{tms}^{CDCl_3}$ 1.00 (t,3,CH$_2$Ch$_3$), 1.75 (broad s,1,NH), 2.60 (q2,CH$_2$CH$_3$), 4.60 (s,2,CH$_2$), 6.70 (s,2,aromatic), 7.37–7.80 (m,4,aromatic), 8.10–8.45 (m,2, aromatic) and 8.70 broad

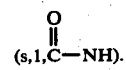

(s,1,C—NH).

Analysis: (C$_{22}$H$_{25}$N$_3$O$_3$). Calculated (percent): C=68.64; H=6.64; N=11.07. Found (percent): C=69.57; H=6.52 N=10.83.

EXAMPLE 2

1-(2-[2-methylamino-acetyl] amino-3,4-dimethoxybenzyl) isoquinoline

Following the procedure of Example 1, but substituting methylamine for ethylamine in part (E), there is obtained 1-(2-[2-methylamino-acetyl] amino-3,4-dimethoxybenzyl) isoquinoline.

EXAMPLE 3

1-(2-[2-n-propylamino-acetyl] amino-3,4-dimethoxybenzyl) isoquinoline

Following the procedure of Example 1, but substituting n-propylamine for ethylamine in part (E), there is obtained 1-(2-[2-n-propylamino-acetyl] amino-3,4-dimethoxybenzyl isoquinoline.

EXAMPLE 4

1-(2-[2-isopropylamino-acetyl] amino-3,4-dimethoxybenzyl) isoquinoline

Following the procedure of Example 1, but substituting isopropylamine for ethylamine in part (E), there is obtained 1-(2-[2-isopropylamino-acetyl] amino-3,4-dimethoxybenzyl) isoquinoline.

EXAMPLE 5

1-(2-[2-methylamino-propionyl] amino-3,4-dimethoxybenzyl) isoquinoline.

Following the procedure of Example 1, but reacting 1-(2-[2-chloro-propionyl] amino-3,4-dimethoxybenzyl) isoquinoline with methylamine, there is obtained 1-(2-[2-methylamino-propionyl] amino-3,4-dimethoxybenzyl)isoquinoline.

EXAMPLE 6

1-(2-[2-ethylamino-propionyl] amino-3,4dimethoxybenzyl) isoquinoline

Following the procedure of Example 1, but reacting 1-(2-[2-chloro-propionyl] amino-3,4-dimethoxybenzyl) isoquinoline with ethylamine, there is obtained 1-(2-[ethylaminoproionyl] amino-3,4-dimethoxybenzyl) isoquinoline.

EXAMPLE 7

1-(2-[2-n-propylamino-propionyl] amino-3,4-dimethoxybenzyl) isoquinoline

Following the procedure of Example 1, but reacting 1-(2-[2-chloro-propionyl] amino-3,4-dimethoxybenzyl) isoquinoline with n-propylamine, there is obtained 1-(2-[2-n-propylaminoprionyl] amino-3,4-dimethoxybenzyl) isoquinoline.

EXAMPLE 8

1-(2-[2-isopropylamino-propionyl] amino-3,4-dimethoxybenzyl) isoquinoline

Following the procedure of Example 1, but reacting 1-(2-[2-chloro-propionyl] amino-3,4-dimethoxybenzyl) isoquinoline with isopropylamine, there is obtained 1-(2[2-isopropylamino-propionyl] amino-3,4-dimethoxybenzyl) isoquinoline.

PHARMACOLOGICAL ACTIVITY

The superior anti-arrhythmic activity of the structure of the invention was demonstrated by comparison with papaverine and lidocaine, representing compounds of known activity, and also with compounds of related benzyl isoquinoline structure, by measurement of protection afforded at various dosage levels against chloroform-induced ventricular fibrillation in mice. Ventricular fibrillation was produced in female Swiss albino mice (Ham/ICR weighing 18-25g.) essentially according to the method described by Lawson in J. Pharm, Exp. Therap. 160, 22 (1968).

The mice were placed individually into a 2,000 ml. beaker with cotton and 50 ml. of chloroform. Immediately after cessation of respiration the mouse was removed from the beaker, the thorax opened and the heart examined for the presence or absence of ventricular fibrillation. Each heart was stimulated by touching with forceps, and the nature of the cardiac rhythm was noted and confirmed by electrocardiographic recordings. The heart was considered to be fibrillating if fine tremulous movements were present on the surface of the ventricle and persisted for at least five seconds after the mechanical stimulus. Ventricular fibrillation was considered absent in those animals in which coordinated ventricular activity was evident following such procedures.

For initial evaluation of antiarrhythmic activity and toxicity of test compounds, a dose of 100 mg/kg (calculated for the base form, 1% solution in 0.9% saline, adjusted to pH 6-7) was administered subcutaneously to a group of 10 non-fasted, randomly selected mice. During 20 minutes the mice were observed for signs of central nervous system toxicity, particularly ataxia, convulsions, and loss of righting reflex. After 20 minutes they were exposed to chloroform vapors and tested for protection against fibrillation.

For determination of $ED_{50}$ and relative potency of the compounds, three log-spaced doses of drug were selected to give a low, intermediate, and high degree of protection against fibrillation. Each doses was administered to 10 mice.

The data obtained from the three point assay was computer-analyzed using Berkson's minimum logit chi square analysis. The program was designed to give $ED_{50}$ values with 95 percent Fieller limits. Relative potency figures were calculated ($ED_{50}^{-1}$ in mmol/kg) and standardized to give a potency of 1 for compound 1.

The structure of the benzyl isoquinoline compounds used in the evaluation is represented by the formula

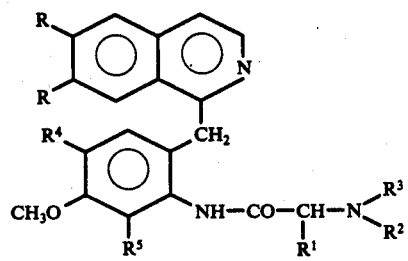

in which
$R, R^4$, and $R^5 = H$ or $CH_3O$
$R^1 = H$ or $CH_3$
$R^2$ and $R^3 = H$ or $C_2H_5$ Results of tests are tabulated according to a numerical series indicating the various combinations of substituents on the structure as follows:

1. $R = R^4 = CH_3O$
   $R^1 = R^5 = H$
   $R^2 = R^3 = C_2H_5$
2. $R = R^4 = CH_3O$
   $R^1 = R^2 = R^5 = H$
   $R^3 = C_2H_5$
3. $R = R^4 = H$
   $R^5 = CH_3O$
   $R^1 = H$
   $R^2 = R^3 = C_2H_5$
4. $R = R^4 = H$
   $R^5 = CH_3O$
   $R^1 = H$
   $R^2 = C_2H_5$
   $R^3 = H$
5. $R = R^4 = H$
   $R^5 = CH_3O$
   $R^1 = CH_3$
   $R^2 = R^3 = H$
6. $R = H$
   $R^4 = CH_3O$
   $R^1 = R^5 = H$
   $R^2 = R^3 = C_2H_5$

The following tetrahydroisoquinoline structure was also included in the evaluation, designated as compound 7:

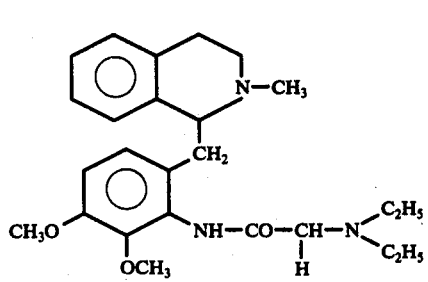

(7)

Comparisons between activity and toxicity, as related to structure of the compounds, under the conditions of the test procedure, are recorded in Table 1. It can be seen that at dosage level of 100 mg/kg, papaverine showed only little antiarrhythmic activity, while producing some evidence of toxicity. Under the same conditions, the strong antiarrhythmic activity of lidocaine was accompanied by high toxicity.

Introduction of the aminoacetamide side chain into the isoquinoline structure increased the antiarrhythmic activity and decreased the central nervous system toxicity as indicated by the test results with compound 1. The corresponding secondary amine, compound 2, provided comparable protection against fibrillation at the same test dose, but evidenced higher toxicity.

The tetrahydroisoquinoline structure, compound 7, as a tertiary amine, provided essentially the same protection, with comparable toxicity characteristics, as compound 1.

Substitution at the 3'-4' position on the benzyl ring produced greater antiarrhythmic activity with lower toxicity than 4'-5' benzyl ring substitution as shown by compound 3 in comparison with compound 6.

The primary amines, as exemplified by compound 5, did not show any outstanding properties, nor was there any notable effect from substitution of an alkyl group at the 2 position.

Secondary amines have generally been of little interest as antiarrhythmic drugs because of central nervous system toxicity found at effective dosage levels. This was illustrated in the present study by the toxicity symptoms accompanying the use of compound 2, and in the literature by the reports of Blumer, Strong, and Atkinson in J. Pharm. and Exp. Therapeutics, 186, 1, 31-36, 1973, that monoethylglycinexylidide, the secondary amine of the lidocaine structure, appears to be the metabolite contributing to the production of the convulsive symptoms of central nervous system toxicity with high doses of lidocaine. Surprisingly, the secondary amine, compound 4, unexpectedly shows a markedly higher antiarrhythmic potency than both its tertiary amine congener, compound 3, and lidocaine. These data, showing $ED_{50}$ values for protecting against fibrillation, and relative potency of comparable test compounds along with lidocaine, are given in Table 2.

Further confirmation of the superiority of the secondary amine compound was provided by comparison of the secondary and tertiary amines in tests on coronary ligated dogs. Data from these tests are shown in Table 3. The tests were conducted in accordance with the procedure of Harris given in Circulation, 1, 1318, 1950. The drugs were administered by the intravenous route by infusion at a dosage of 0.5 mg./kg./minute, in a volume of 0.97 ml./minute and a concentration of 5.2-4.3 mg/ml. The animals were weighed and the solutions prepared on the day of the experiment.

While it can be seen that both the tertiary amine, compound 3, and the secondary amine, compound 4, were effective in abolishing severe arrhythmias, the preferred structure of the invention, compound 4, did so at doses that were free from indications of central nervous system and cardiovascular toxicity.

The tests, therefore, demonstrate that the structure of the invention has significantly greater antiarrhythmic potency and lower central nervous system and cardiovascular toxicity than drugs currently employed.

The invention may be variously otherwise embodied within the scope of the appended claims.

TABLE 1

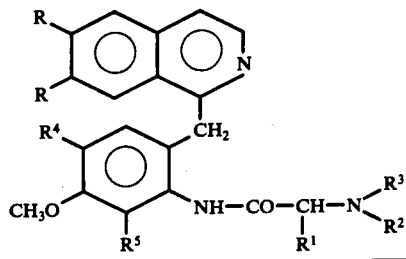

ANTIARRHYTHMIC EFFECT AND TOXICITY IN MICE

| COM-POUND | Dose mg/kg | Number Protected | Ataxia | Con.[1] | LRR[2] | Death |
|---|---|---|---|---|---|---|
| Lidocaine | 100 | 10 | 10 | 10 | 10 | 0 |
| Papaverine | 100 | 2 | 2 | 0 | 0 | 0 |
| 1 | 100 | 6 | 0 | 0 | 0 | 0 |
| 2 | 100 | 5 | 9 | 0 | 0 | 0 |
| 3 | 100 | 6 | 0 | 0 | 0 | 0 |
| 4 | 100 | 7 | 0 | 0 | 0 | 0 |
| 5 | 100 | 1 | 0 | 0 | 0 | 0 |
| 6 | 100 | 2 | 7 | 0 | 0 | 0 |
| 7 | 138 | 5 | 0 | 0 | 0 | 0 |

[1] = Convulsions
[2] = Loss of righting reflex (1) $R=R^4=CH_3O$
$R^1=R^5=H$
$R^2=R^3=C_2H_5$ (2) $R=R^4=CH_3O$
$R^1=R^2=R^5=H$
$R^3=C_2H_5$ (3) $R=R^4=H$
$R^5=CH_3O$
$R^1=H$
$R^2=R^3=C_2H_5$ (4) $R=R^4=H$
$R^5=CH_3O$
$R^1=H$
$R^2=C_2H_5$
$R^3=H$ (5) $R=R^4=H$
$R^5=CH_3O$
$R^1=CH_3$
$R^2=R^3=H$ (6) $R=H$
$R^4=CH_3O$
$R^1=R^5=H$
$R^2=R^3=C_2H_5$ (7) 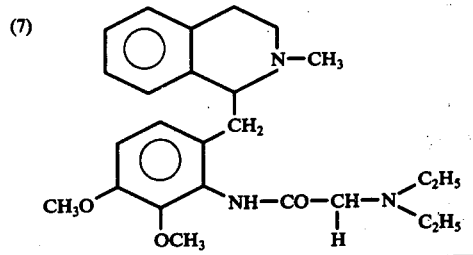

TABLE 2

$ED_{50}$ FOR PROTECTING AGAINST FIBRILLATION, AND DETERMINED RELATIVE POTENCY IN MICE.

| | ANTIARRHYTHMIC EFFECT | |
|---|---|---|
| COMPOUND | $ED_{50}$ mg/kg | Relative Potency (molar basis) |
| Lidocaine | 62* | 2 |
| 1 | 211 (124-360) | 1 |
| 2 | 142 (61-330) | 1 |
| 3 | 146 (103-436) | 1 |
| 4 | 54 (38-86) | 3 |
| 5 | 257 (153-634) | 1 |
| 7 | 160 (104-222) | 1 |

*Mean of 125 determinations
95% Fieller limits shown in brackets

TABLE 3

ANTIARRHYTHMIC EFFECT AND TOXICITY IN DOGS, INTRAVENOUS ADMINISTRATION

| | CONTROL VALUES | | | VALUES AFTER ADMINISTRATION | | | DOSE (mg/kg) | |
|---|---|---|---|---|---|---|---|---|
| COMPOUNDS | Percent Ventricular Ectopic Beats | Ventricular Rate | Mean Arterial Blood Pressure | Percent Ventricular Ectopic Beats | Ventricular Rate | Mean Arterial Blood Pressure | Dose Producing Clearing | Dose Producing Toxicity |
| 3 | 95 | 189 | 80 | 9 | 153 | 100 | 46.5 | 12.5[a] |

TABLE 3-continued

| | ANTIARRHYTHMIC EFFECT AND TOXICITY IN DOGS, INTRAVENOUS ADMINISTRATION | | | | | | | |
|---|---|---|---|---|---|---|---|---|
| | CONTROL VALUES | | | VALUES AFTER ADMINISTRATION | | | DOSE (mg/kg) | |
| COMPOUNDS | Percent Ventricular Ectopic Beats | Ventricular Rate | Mean Arterial Blood Pressure | Percent Ventricular Ectopic Beats | Ventricular Rate | Mean Arterial Blood Pressure | Dose Producing Clearing | Dose Producing Toxicity |
| | 93 | 221 | 92 | 0 | 135 | 90 | 52 | 6.25(a) 15.75(b) |
| 4 | 84 | 126 | 115 | 1 | 147 | 125 | 10 | (c) |
| | 98 | 186 | 100 | 0 | 123 | 85 | 45 | |

(a) = profound head tremors
(b) = convulsion
(c) = no toxic effects at dose which caused clearing

We claim:
1. A compound having the formula

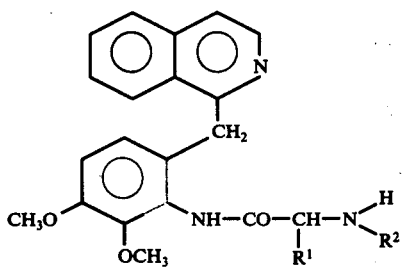

wherein R¹ is selected from the group consisting of hydrogen and methyl, and R² is selected from the group consisting of methyl, ethyl, n-propyl, and isopropyl, and therapeutically acceptable acid addition salts thereof.

2. A compound according to claim 1, 1-(2-[2-ethylamino-acetyl] amino-3,4-dimethoxybenzyl) isoquinoline.

3. A compound according to claim 1, 1-(2-[2-methylamino-acetyl] amino-3,4-dimethoxybenzyl) isoquinoline.

4. A compound according to claim 1, 1-(2-[2-n-propylamino-acetyl] amino-3,4-dimethoxybenzyl) isoquinoline.

5. A compound according to claim 1, 1-(2-[2-isopropylamino-acetyl] amino-3,4-dimethoxybenzyl) isoquinoline.

6. A compound according to claim 1, 1(2-[2-methylamino-propionyl] amino-3,4-dimethoxybenzyl) isoquinoline.

7. A compound according to claim 1, 1-(2-[2-ethyalmino-propionyl] amino-3,4-dimethoxybenzyl) isoquinoline.

8. A compound according to claim 1, 1-(2-[2-n-propylamino-propionyl] amino-3,4-dimethoxybenzyl) isoquinoline.

9. A compound according to claim 1, 1-(2-[2-isopropylamino-propionyl] amino-3,4-dimethoxybenzyl) isoquinoline.

10. A pharmaceutical preparation for the suppression of cardiac arrhythmias comprising as an active ingredient an amount effective for the suppression of cardiac arrhythmias of a compound having the formula

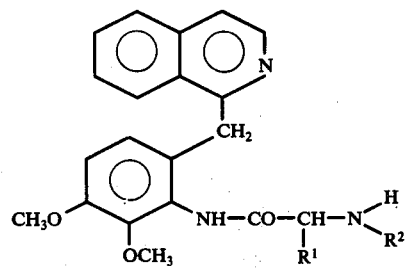

wherein R¹ is selected from the group consisting of hydrogen and methyl, and R² is selected from the group consisting of methyl, ethyl, n-propyl, and isopropyl, and therapeutically acceptable acid addition salts thereof, in association with a pharmaceutically and therapeutically acceptable carrier.

11. A preparation according to claim 10, wherein the active ingredient is 1-(2-[2-ethylamino-acetyl] amino-3,4-dimethoxybenzyl) isoquinoline, or a therapeutically acceptable acid addition salt thereof.

12. A preparation according to claim 10, wherein the active ingredient is 1-(2-[2-methylamino-acetyl] amino-3,4-dimethyoxybenzyl) isoquinoline, or a therapeutically acceptable acid addition salt thereof.

13. A preparation according to claim 10, wherein the active ingredient is 1-(2-[2-n-propylamino acetyl] amino-3,4-dimethoxybenzyl) isoquinoline, or a therapeutically acceptable acid addition salt thereof.

14. A preparation according to claim 10, wherein the active ingredient is 1-(2-[2-isopropylamino-acetyl] amino-3,4-dimethoxybenzyl) isoquinoline, or a therapeutically acceptable acid addition salt thereof.

15. A preparation according to claim 10, wherein the active ingredient is 1-(2-[2-methylamino-propionyl] amino-3,4-dimethoxybenzyl) isoquinoline, or a therapeutically acceptable acid addition salt thereof.

16. A preparation according to claim 10, wherein the active ingredient is 1-(2-[2-ethylamino-propionyl] amino-3,4-dimethoxybenzyl) isoquinoline, or a therapeutically acceptable acid addition salt thereof.

17. A preparation according to claim 10, wherein the active ingredient is 1-(2-[2-n-propylamino-propionyl] amino-3,4-dimethoxybenzyl) isoquinoline, or a therapeutically acceptable acid addition salt thereof.

18. A preparation according to claim 10, wherein the active ingredient is 1-(2-[2-isopropylamino-propionyl] amino-3,4-dimethoxybenzyl) isoquinoline, or a therapeutically acceptable acid addition salt thereof.

19. A process for the suppression of cardiac arrhythmias in mammals comprising administering to the mammal an amount effective for the suppression of cardiac arrhythmias of a compound having the formula

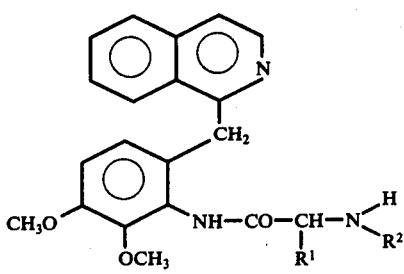

wherein R¹ is selected from the group consisting of hydrogen and methyl, and R² is selected from the group consisting of methyl, ethyl, n-propyl, and isopropyl, and therapeutically acceptable salts thereof.

20. A process according to claim 19, wherein the compound administered is 1-(2-[2-ethylamino-acetyl] amino-3,4-dimethoxybenzyl) isoquinoline, or a therapeutically acceptable acid addition salt thereof.

21. A process according to claim 19, wherein the compound administered is 1-(2-[2-methylamino-acetyl] amino-3,4-dimethoxybenzyl) isoquinoline, or a therapeutically acceptable acid addition salt thereof.

22. A process according to claim 19, wherein the compound administered is 1-(2-[2-n-propylamino-acetyl] amino-3,4-dimethoxybenzyl) isoquinoline, or a therapeutically acceptable acid addition salt thereof.

23. A process according to claim 19, wherein the compound administered is 1-(2-[2-isopropylamino-acetyl] amino-3,4-dimethoxybenzyl) isoquinoline, or a therapeutically acceptable acid addition salt thereof.

24. A process according to claim 19, wherein the compound administered is 1-(2-[2-methylamino-propionyl] amino-3,4-dimethoxybenzyl) isoquinoline, or a therapeutically acceptable acid addition salt thereof.

25. A process according to claim 19, wherein the compound administered is 1-(2-[2-ethylamino-propionyl] amino-3,4-dimethoxybenzyl) isoquinoline, or a therapeutically acceptable acid addition salt thereof.

26. A process according to claim 19, wherein the compound administered is 1-(2-[2-n-propylamino-propionyl] amino-3,4-dimethoxybenzyl) isoquinoline, or a therapeutically acceptable acid addition salt thereof.

27. A process according to claim 19, wherein the compound administered is 1-(2-[2-isopropylamino-propionyl] amino-3,4-dimethoxybenzyl) isoquinoline, or a therapeutically acceptable acid addition salt thereof.

* * * * *

UNITED STATES PATENT AND TRADEMARK OFFICE
CERTIFICATE OF CORRECTION

PATENT NO. : 4,053,603
DATED : October 11, 1977
INVENTOR(S) : John Leopold Neumeyer and Paul Andre Tenthorey It is certified that error appears in the above-identified patent and that said Letters Patent are hereby corrected as shown below:

Col. 1, line 59, "porcainamide" should be --procainamide--.
Col. 1, line 66, "incudes" should be --includes--.
Col. 2, line 44, after "or" insert --a--.
Col. 6, line 1, "compounding" should read --compound--.
Col. 7, line 38, "aminde" should read --amide--.
Col. 8, line 1, "(q2,CH2CH3)" should read --(q,2,CH$_2$CH$_3$)--.
Col. 8, line 10, "68.64" should read --69.64--.
Col. 8, line 53, "3,4dimethoxybenzyl)" should read
    --3,4-dimethoxybenzyl)--.
Col. 8, lines 56 and 57, "[ethylaminoproionyl]" should read
    --[ethylaminopropionyl]--.
Col. 8, line 67, "propylaminoprionyl" should read
    --propylaminopropionyl--.
Col. 9, line 9, "1-(2[2-" should read --1-(2-[2- --.
Col. 9, line 58, "doses" should read --dose--.
Col. 9, line 65, "(ED$_{50}$-1" should read --(ED$_{50}^{1}$ --.

Col. 13, line 53, "1(2-[2-" should read --1-(2-[2- --.
Col. 13, lines 56 and 57, "ethyalmino" should read --ethylamino--.
Col. 14, line 42, "propylamino acetyl" should read
    --propylamino-acetyl--.

Signed and Sealed this

Eighth Day of August 1978

[SEAL]

Attest:

RUTH C. MASON
Attesting Officer

DONALD W. BANNER
Commissioner of Patents and Trademarks